(12) United States Patent
Jiaang et al.

(10) Patent No.: US 10,047,078 B2
(45) Date of Patent: Aug. 14, 2018

(54) AMINOTHIAZOLE COMPOUNDS

(71) Applicant: National Health Research Institutes, Miaoli County (TW)

(72) Inventors: Weir-Torn Jiaang, Taipei (TW); Tsu Hsu, Taipei (TW)

(73) Assignee: National Health Research Institutes, Zhunan Town (TW)

( * ) Notice: Subject to any disclaimer, the term of this patent is extended or adjusted under 35 U.S.C. 154(b) by 0 days.

(21) Appl. No.: 15/419,183

(22) Filed: Jan. 30, 2017

(65) Prior Publication Data
US 2017/0226100 A1 Aug. 10, 2017

Related U.S. Application Data

(60) Provisional application No. 62/291,667, filed on Feb. 5, 2016.

(51) Int. Cl.
*C07D 417/14* (2006.01)
(52) U.S. Cl.
CPC ................. *C07D 417/14* (2013.01)
(58) Field of Classification Search
CPC .................................................. C07D 417/14
See application file for complete search history.

(56) References Cited

U.S. PATENT DOCUMENTS

| | | |
|---|---|---|
| 8,372,849 B2 | 2/2013 | Yen et al. |
| 2012/0225880 A1 | 9/2012 | Jiaang et al. |
| 2013/0150364 A1 | 6/2013 | Takahashi et al. |

FOREIGN PATENT DOCUMENTS

| | | |
|---|---|---|
| WO | WO 2010/046780 | 4/2010 |
| WO | WO 2013/046136 | 4/2013 |

OTHER PUBLICATIONS

Chen, et al., "Identification of a potent 5-phenyl-thiazol-2-ylamine-based inhibitor of FLT3 with activity against drug resistance-conferring point mutations", European Journal of Medicinal Chemistry 100 (2015) pp. 151-161.

Patani et al "Bioisosterism: A Rational Approach in Drug Design" Chemical Reviews vol. 96, pp. 3147-3176, 1996.

*Primary Examiner* — Rebecca L Anderson
(74) *Attorney, Agent, or Firm* — Cesari and McKenna, LLP

(57) ABSTRACT

Aminothiazole compounds of Formula (I) shown herein and pharmaceutical compositions containing one of such compounds.

22 Claims, No Drawings

AMINOTHIAZOLE COMPOUNDS

CROSS REFERENCE TO RELATED APPLICATIONS

The present application claims priority to U.S. Provisional Application No. 62/291,667, filed on Feb. 5, 2016. The content of that application is hereby incorporated by reference in its entirety.

BACKGROUND

Protein kinases are important in cellular signal pathways that regulate various cell functions, including differentiation, proliferation, migration, and apoptosis. Deregulation of protein kinases is implicated in cancer and a number of other diseases.

Heterocyclic compounds have been extensively studied as potent protein kinase inhibitors. Among various classes of heterocyclic compounds, aminothiazoles appear as a recurring structural motif in many biologically active compounds.

As drug candidates, aminothiazoles present several challenges. First, they generally lack adequate in vivo exposure to exert desirable efficacy in pre-clinical or clinical studies. Further, being promiscuous protein kinase inhibitors, aminothiazoles possess poor kinase selectivity. Moreover, they often cause animal death in toxicity studies, raising safety concerns.

There is a need to develop new aminothiazoles that effectively inhibit certain protein kinases, exert sufficient in vivo efficacy in treating target diseases, and demonstrate desirable safety profiles.

SUMMARY

The present invention is based on unexpected discoveries that certain aminothiazole compounds inhibit multiple protein kinases effectively, exert high in vivo anti-cancer efficacy, and show great safety.

In one aspect, this invention relates to aminothiazole compounds of Formula (I):

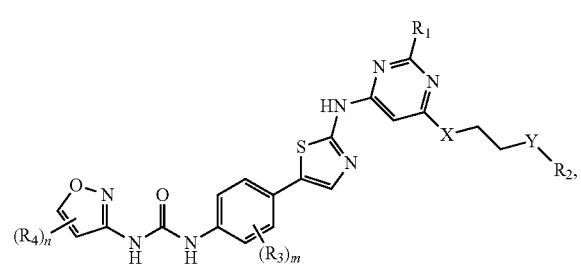

in which $R_1$ is H; X is O or $NR_a$, $R_a$ being H or $C_{1-6}$ alkyl; Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl; $R_2$ is —$CH_2CH_2R_e$ or $NR_fR_g$, in which $R_e$ is H, halo, $C_{1-6}$ alkyl, or $OR_h$, each of $R_f$ and $R_g$, independently, being $C_{1-6}$ alkyl or $C_{3-8}$ cycloalkyl, and $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; each of $R_3$ and $R_4$, independently, is H, halo, nitro, cyano, amino, $C_{1-6}$ alkyl, $C_{1-6}$ alkoxyl, $C_{3-10}$ cycloalkyl, $C_{3-10}$ heterocycloalkyl, aryl, or heteroaryl; m is 1, 2, 3, or 4; and n is 1 or 2.

In another aspect, this invention relates to aminothiazole compounds of Formula (I), in which $R_1$ is $C_{1-6}$ alkyl or $C_{1-6}$ thioalkyl; X is O or $NR_a$, $R_a$ being H or $C_{1-6}$ alkyl; Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl; $R_2$ is —$CH_2CH_2R_e$ or $NR_fR_g$, in which $R_e$ is halo, $C_{1-6}$ alkyl, or $OR_h$, each of $R_f$ and $R_g$, independently, being $C_{1-6}$ alkyl or $C_{3-8}$ cycloalkyl, and $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; $R_3$ is H, halo, nitro, cyano, amino, $C_{1-6}$ alkyl, $C_{1-6}$ alkoxyl, $C_{3-10}$ cycloalkyl, $C_{3-10}$ heterocycloalkyl, aryl, or heteroaryl; $R_4$ is halo, cyano, $C_{2-6}$ alkyl, $C_{2-6}$ alkoxyl, $C_{3-10}$ cycloalkyl, $C_{3-10}$ heterocycloalkyl, aryl, or heteroaryl; m is 1, 2, 3, or 4; and n is 1 or 2.

The term "alkyl" herein refers to a saturated, linear or branched hydrocarbon moiety, such as —$CH_3$ or branched —$C_3H_7$. The term "cycloalkyl" refers to a non-aromatic, monocyclic, bicyclic, tricyclic, or tetracyclic hydrocarbon moiety, such as cyclohexyl, cyclohexen-3-yl, or adamantyl. The term "alkoxyl" refers to an —O-alkyl radical. Examples of alkoxyl include, but are not limited to, methoxy, ethoxy, n-propoxy, isopropoxy, n-butoxy, iso-butoxy, sec-butoxy, and tert-butoxy. The term "thioalkyl" refers to an —S-alkyl radical. Examples of thioalkyl include, but are not limited to, methylthiol, ethylthiol, and benzylthiol. The term "heterocycloalkyl" refers to a non-aromatic, monocyclic, bicyclic, tricyclic, or tetracyclic moiety having one or more ring heteroatoms (e.g., N, O, or S). Examples of heterocycloalkyl include, but are not limited to, 4-morpholinyl, 1-piperazinyl, 4-tetrahydropyranyl, and 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, thioalkyl, alkoxyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include $C_{1-10}$ alkyl, $C_{2-10}$ alkenyl, $C_{2-10}$ alkynyl, $C_{3-20}$ cycloalkyl, $C_{3-20}$ cycloalkenyl, $C_{1-20}$ heterocycloalkyl, $C_{1-20}$ heterocycloalkenyl, $C_{1-10}$ alkoxy, aryl, aryloxy, heteroaryl, heteroaryloxy, amino, $C_{1-10}$ alkylamino, $C_{1-20}$ dialkylamino, arylamino, diarylamino, hydroxyl, halogen, thio, $C_{1-10}$ alkylthio, arylthio, $C_{1-10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl include all of the above-recited substituents except $C_{1-10}$ alkyl, $C_{2-10}$ alkenyl, and $C_{2-10}$ alkynyl. Cycloalkyl, heterocycloalkyl, aryl, and heteroaryl can also be fused with each other.

The aminothiazole compounds described above include the compounds themselves, as well as their salts, prodrugs, and solvates, if applicable. A salt, for example, can be formed between an anion and a positively charged group (e.g., amino) on an aminothiazole compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an aminothiazole compound. Suitable cations include sodium ion, potassium ion, magnesium ion, calcium ion, and an ammonium cation such as tetramethylammonium ion. The aminothiazole compounds also include those salts containing quaternary nitrogen atoms. Examples of prodrugs include esters and other pharmaceutically acceptable derivatives, which, upon administering to a subject, are capable of providing active aminothiazole compounds. A solvate refers to a complex formed between an active aminothiazole compound and a pharmaceutically acceptable solvent. Examples of a pharmaceutically acceptable solvent include water, ethanol, isopropanol, ethyl acetate, acetic acid, and ethanolamine.

In still another aspect, this invention relates to a method for inhibiting a protein kinase. The method includes contacting the protein kinase with an effective amount of one or more of the above-described aminothiazole compounds.

Also within the scope of this invention is a method for treating cancer associated with a is protein kinase. The method includes administering to a subject in need thereof an effective amount of one or more of the aminothiazole compounds of Formula (I) described above.

The protein kinase can be a wild type or mutant. Examples of the protein kinase include FMS-like tyrosine kinase 3 (FLT3), FMS-like tyrosine kinase 4 (FLT4), aurora kinase (AURK) A, AURK B, vascular endothelial growth factor receptor (VEGFR), platelet-derived growth factor receptor (PDGFR) A, PDGFR B, c-Src (SRC), tyrosine-protein kinase Lyn (LYN) A, LYN B, rearranged during transfection tyrosine kinase (RET), colony stimulating factor 1 receptor (CSF1R), lymphocyte-specific protein tyrosine kinase (LCK), Gardner-Rasheed feline sarcoma viral (v-fgr) oncogene homolog (FGR), discoidin domain receptor 1 (DDR1), kinase insert domain receptor (KDR), tropomyosin receptor kinase (TRK) A, TRK B, B lymphocyte kinase (BLK), tyrosine-protein kinase Yes (YES1), Abelson murine leukemia viral oncogene homolog 1 (ABL1), tyrosine-protein kinase Kit (KIT), dual specificity mitogen-activated protein kinase kinase 1 (MEK1), interleukin-1 receptor-associated kinase 4 (IRAK4), tyrosine-protein kinase Tek (TEK), RET V804L, RET Y791F, FLT3 D835Y, PDGFR A V561D, and ABL1 T315I.

Examples of the cancer include acute myeloid leukemia, chloroma, chronic myelogenous leukemia, acute lymphoblastic leukemia, chronic lymphocytic leukemia, Hodgkin's disease, non-Hodgkin's lymphoma, B-cell lymphoma, multiple myeloma, Waldenstrom's macroglobulinemia, myelodysplastic syndrome, pancreatic cancer, bladder cancer, colorectal cancer, breast cancer, male genital tract cancer, renal cancer, hepatocellular cancer, lung cancer, ovarian cancer, cervical cancer, uterus cancer, gestational trophoblastic disease, gastric cancer, bile duct cancer, gallbladder cancer, small intestine cancer, esophageal cancer, oropharyngeal cancer, hypopharyngeal cancer, eye cancer, nerve cancer, head and neck cancer, melanoma, plasmacytoma, endocrine gland neoplasm, neuroendocrine cancer, brain tumor, bone cancer, and sarcoma.

Further within the scope of this invention is a pharmaceutical composition containing one or more of the above-described aminothiazole compounds of Formula (I). The pharmaceutical composition can be used for treating cancer.

This invention also encompasses use of one or more of the above-described aminothiazole compounds of Formula (I) for the manufacture of a medicament for treating cancer.

The term "treating" or "treatment" refers to administering one or more of the aminothiazole compounds to a subject, who has an above-described disease, i.e., cancer, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it. "An effective amount" refers to the amount of an active compound that is required to confer the therapeutic effect. Effective doses will vary, as recognized by those skilled in the art, depending on the types of disease treated, route of administration, excipient usage, and the possibility of co-usage with other therapeutic treatment.

To practice the method of the present invention, a composition having one or more of the above-described aminothiazole compounds can be administered parenterally, orally, nasally, rectally, topically, or buccally. The term "parenteral" as used herein refers to subcutaneous, intracutaneous, intravenous, intraperitoneal, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives are useful in the preparation of injectables, as are natural pharmaceutically acceptable oils, such as olive oil and castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more of the above-described aminothiazole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The details of one or more embodiments of the invention are set forth in the description below. Other features, objects, and advantages of the invention will be apparent from the description and from the claims.

DETAILED DESCRIPTION

Disclosed are aminothiazole compounds of Formula (I):

(I)

Referring to this formula, two sets of aminothiazole compounds include (i) those in is which $R_1$ is H; X is O or $NR_a$, $R_a$ being H or $C_{1-6}$ alkyl; Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl; $R_2$ is —$CH_2CH_2R_e$ or $NR_fR_g$, in which $R_e$ is H, halo, $C_{1-6}$ alkyl, or $OR_h$, each of $R_f$ and $R_g$, independently, being $C_{1-6}$ alkyl or $C_{3-8}$ cycloalkyl, and $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; each of $R_3$ and $R_4$, independently, is H, halo, nitro, cyano, amino, $C_{1-h}$ alkyl, $C_{1-6}$ alkoxyl, $C_{3-10}$ cycloalkyl, $C_{3-10}$ heterocycloalkyl, aryl, or heteroaryl; m is 1, 2, 3, or 4; and n is 1 or 2; and (ii) those in which $R_1$ is $C_{1-6}$ alkyl or $C_{1-6}$ thioalkyl; X is O or $NR_a$, $R_a$ being H or $C_{1-6}$ alkyl; Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl; $R_2$ is —$CH_2CH_2R_e$ or $NR_fR_g$, in which $R_e$ is halo, $C_{1-6}$ alkyl, or $OR_h$, each of $R_f$ and $R_g$, independently, being $C_{1-6}$ alkyl or $C_{3-8}$ cycloalkyl, and $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl; $R_3$ is H, halo, nitro, cyano, amino, $C_{1-6}$ alkyl, $C_{1-6}$ alkoxyl, $C_{3-10}$ cycloalkyl, $C_{3-10}$ heterocycloalkyl, aryl, or heteroaryl; $R_4$ is halo, cyano, $C_{2-6}$ alkyl, $C_{2-6}$ alkoxyl, $C_{3-10}$ cycloalkyl, $C_{3-10}$ heterocycloalkyl, aryl, or heteroaryl; m is 1, 2, 3, or 4; and n is 1 or 2.

In one embodiment, the aminothiazole compounds set forth above are compounds of Formula (II):

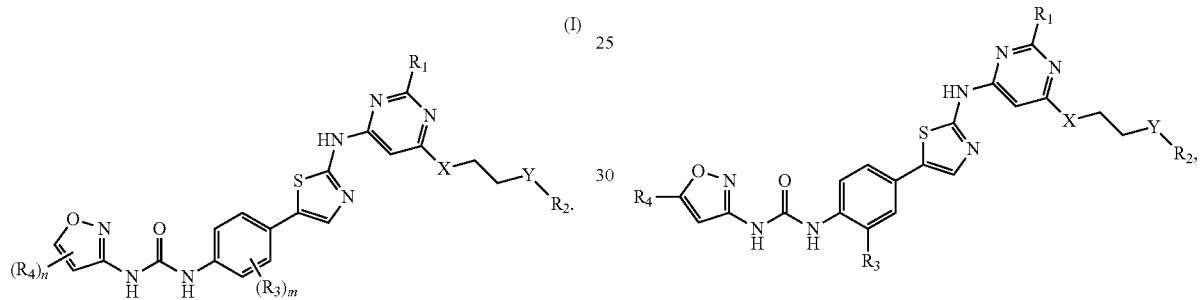

(II)

in which $R_1$, $R_2$, $R_3$, $R_4$, X, and Y are defined as those described in Formula (I) above, both sets.

In one subgroup, compounds of Formula (II) have $R_1$ as H and X as O. Preferably, Y is $NR_d$ and $R_2$ is —$CH_2CH_2R_e$, in which $R_e$ is $OR_h$, $R_h$, together with $R_d$, the oxygen atom bonded to $R_h$, and the nitrogen atom bonded to $R_d$, being $C_{3-10}$ heterocycloalkyl; $R_3$ is H, halo, or $C_{1-6}$ alkyl; and $R_4$ is $C_{1-6}$ alkyl or $C_{3-10}$ cycloalkyl. An exemplary compound is

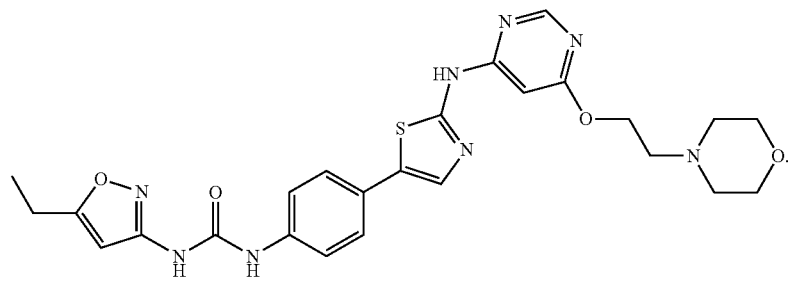 [SMILES: CCc1cc(NC(=O)Nc2ccc(-c3cnc(Nc4cc(OCCN5CCOCC5)ncn4)s3)cc2)no1]

In another subgroup, compounds of Formula (II) have $R_1$ as H and X as $NR_a$, $R_a$ being H or $C_{1-6}$ alkyl. In particular, some compounds in this subgroup have Y as $CR_bR_c$, in which $R_b$, together with $R_a$, the carbon atom bonded to $R_b$, and the nitrogen atom bonded to $R_a$, is $C_{3-10}$ heterocycloalkyl, and $R_c$ is H, halo, $C_{1-6}$ alkyl, $C_{1-6}$ alkoxyl, or amino; $R_2$ as $NR_fR_g$, each of $R_f$ and $R_g$, independently, being $C_{1-6}$ alkyl or $C_{3-8}$ cycloalkyl; $R_3$ as H, halo, $C_{1-6}$ alkyl, or $C_{3-10}$ cycloalkyl; and $R_4$ as $C_{1-6}$ alkyl or $C_{3-10}$ cycloalkyl. Preferably, $R_b$, together with $R_a$, the carbon atom bonded to $R_b$, and the nitrogen atom bonded to $R_a$, is pyrrolidinyl or piperidinyl. Other compounds in this subgroup have Y as $NR_d$, in which $R_d$, together with $R_a$ and the nitrogen atoms bonded to $R_d$ and $R_a$, is $C_{3-10}$ heterocycloalkyl; $R_2$ as —$CH_2CH_2R_e$, in which $R_e$ is H, halo, $C_{1-6}$ alkyl, or $OR_h$, $R_h$ being H or $C_{1-6}$ alkyl; $R_3$ as H, halo, $C_{1-6}$ alkyl, or $C_{3-10}$ cycloalkyl; and $R_4$ as $C_{1-6}$ alkyl or $C_{3-10}$ cycloalkyl. Preferably, $R_d$, together with $R_a$ and the nitrogen atoms bonded to $R_d$ and $R_a$, is piperazinyl. Examples of this group of compounds include

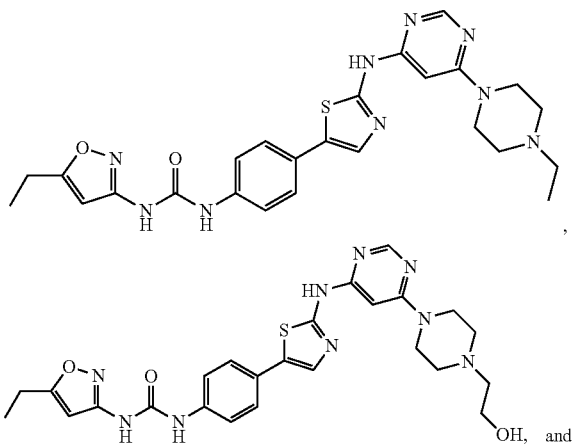

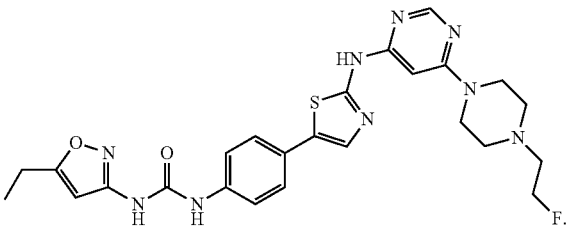

In still another subgroup, compounds of Formula (II) have $R_1$ as $C_{1-6}$ alkyl (e.g., —$CH_3$) or $C_{1-6}$ thioalkyl (e.g., —$SCH_3$) and X as O.

In an additional subgroup, compounds of Formula (II) have $R_1$ as $C_{1-6}$ alkyl (e.g., —$CH_3$) or $C_{1-6}$ thioalkyl (e.g., —$SCH_3$) and X as $NR_a$, $R_a$ being H or $C_{1-6}$ alkyl. In particular, some compounds in this additional subgroup have Y as $CR_bR_c$, in which $R_b$, together with $R_a$, the carbon atom bonded to $R_b$, and the nitrogen atom bonded to $R_a$, is $C_{3-10}$ heterocycloalkyl, and $R_c$ is H, halo, $C_{1-6}$ alkyl, $C_{1-6}$ alkoxyl, or amino; $R_2$ as $NR_fR_g$, each of $R_f$ and $R_g$, independently, being $C_{1-6}$ alkyl or $C_{3-8}$ cycloalkyl; $R_3$ as H, halo, $C_{1-6}$ alkyl, or $C_{3-10}$ cycloalkyl; and $R_4$ as $C_{1-6}$ alkyl or $C_{3-10}$ cycloalkyl. Preferably, $R_b$, together with $R_a$, the carbon atom bonded to $R_b$, and the nitrogen atom bonded to $R_a$, is pyrrolidinyl or piperidinyl. Exemplary compounds include

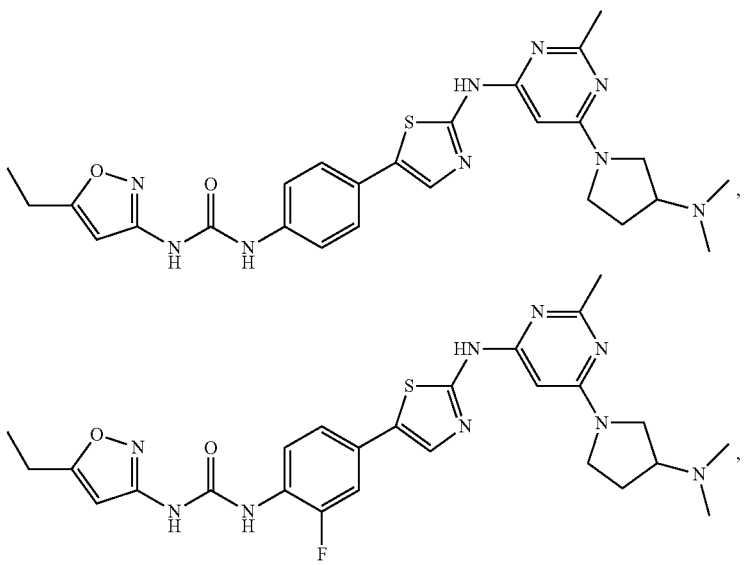

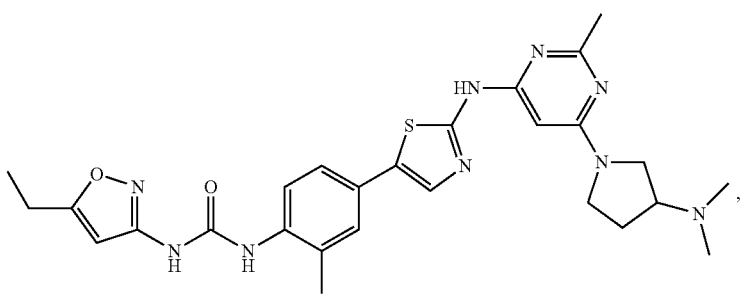

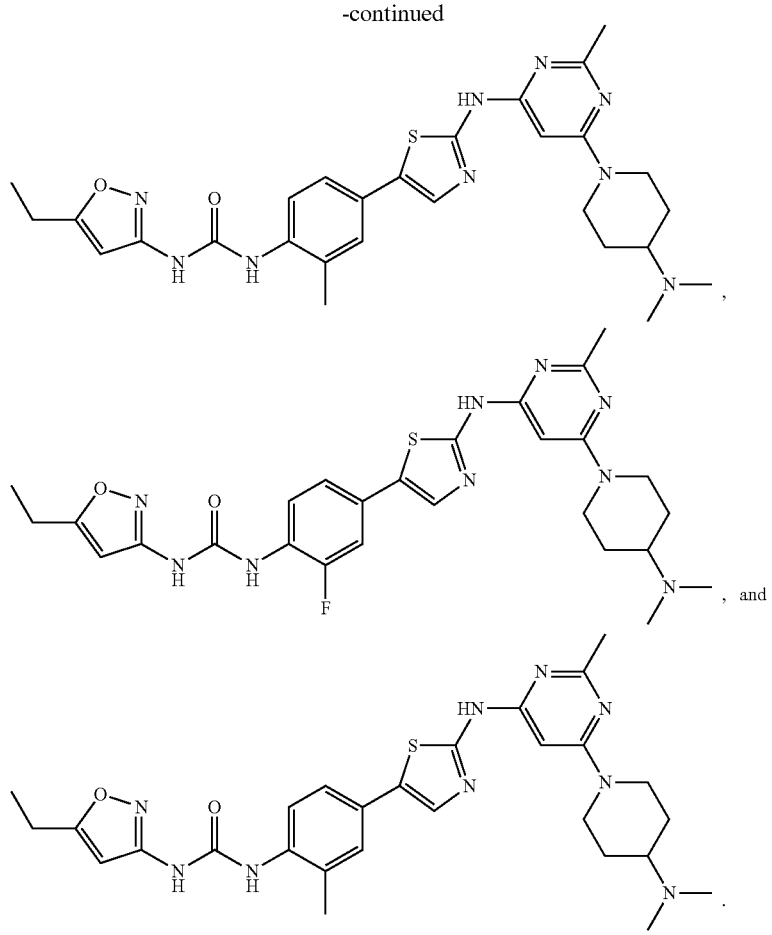

Other compounds in this additional subgroup have Y as $NR_d$, in which $R_d$, together with $R_a$ and the nitrogen atoms bonded to $R_d$ and $R_a$, is $C_{3-10}$ heterocycloalkyl; $R_2$ as —$CH_2CH_2R_e$, in which $R_e$ is halo, $C_{1-6}$ alkyl, or $OR_h$, $R_h$ being H or $C_{1-6}$ alkyl; $R_3$ as H, halo, $C_{1-6}$ alkyl, or $C_{3-10}$ cycloalkyl; and $R_4$ as $C_{1-6}$ alkyl or $C_{3-10}$ cycloalkyl. Preferably, $R_d$, together with $R_a$ and the nitrogen atoms bonded to $R_d$ and $R_a$, is piperazinyl. Examples include -continued

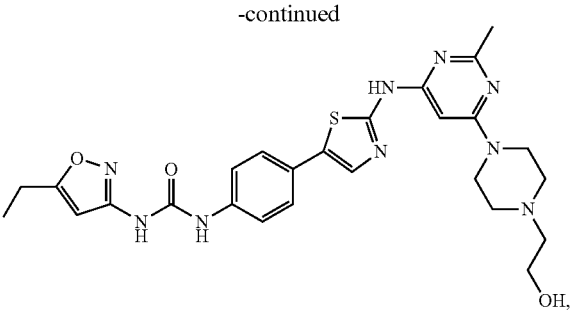

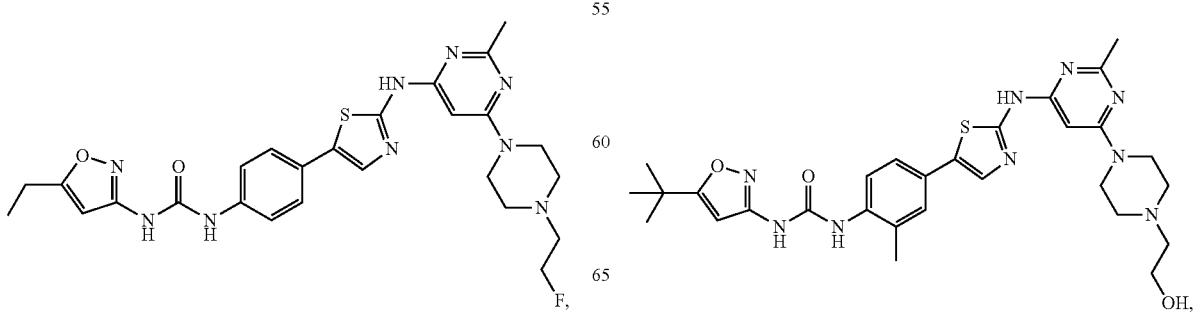

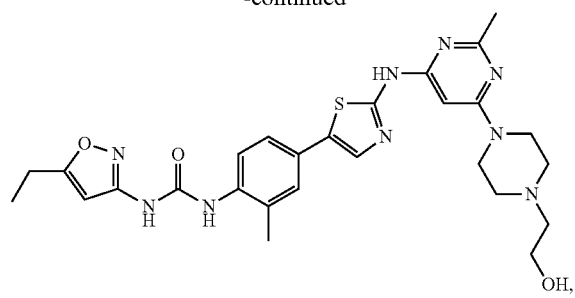
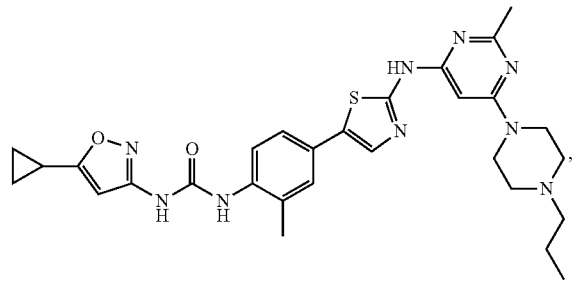
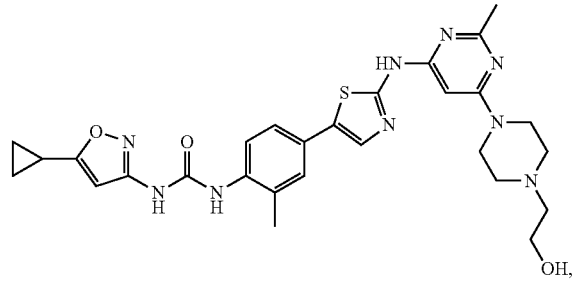
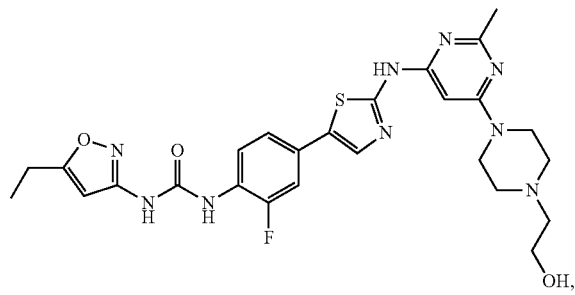
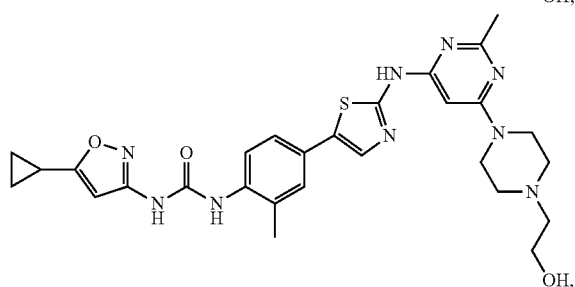
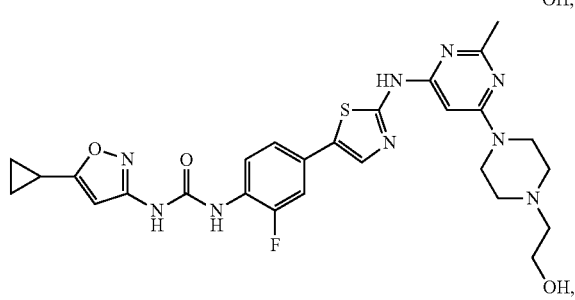

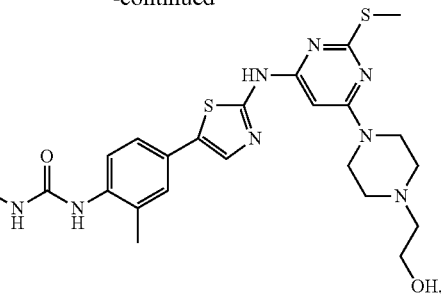
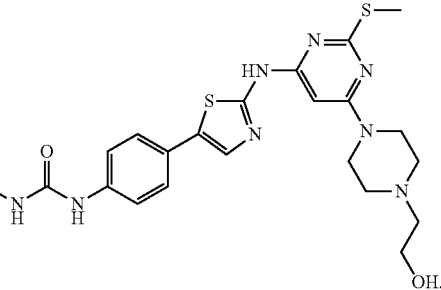
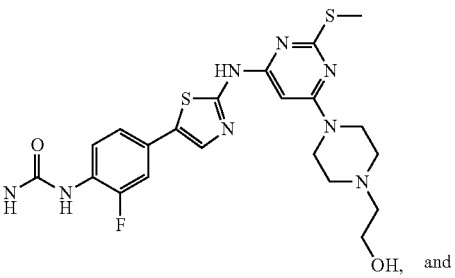
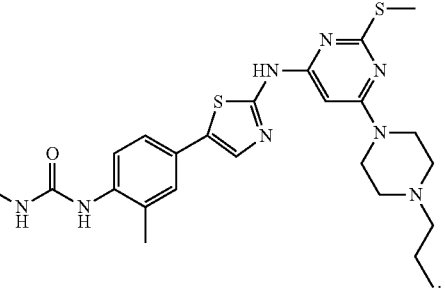
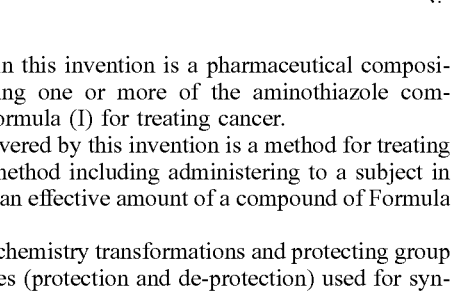

Also within this invention is a pharmaceutical composition containing one or more of the aminothiazole compounds of Formula (I) for treating cancer.

Further covered by this invention is a method for treating cancer, the method including administering to a subject in need thereof an effective amount of a compound of Formula (I).

Synthetic chemistry transformations and protecting group methodologies (protection and de-protection) used for synthesizing the compounds of Formula (I) are well known in the art. See, for example, R. Larock, Comprehensive Organic Transformations (2$^{nd}$ Ed., VCH Publishers 1999); P. G. M. Wuts and T. W. Greene, Greene's Protective Groups in Organic Synthesis (4$^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis (2$^{nd}$ ed., John Wiley and Sons 2009); and G. J. Yu et al., *J. Med. Chem.* 2008, 51, 6044-6054.

The compounds of Formula (I) thus prepared can be initially screened using biochemical assays, e.g., the kinase assay described in Example 21 below, for their potency in inhibiting protein kinases. They can be subsequently evaluated using in vivo assays, e.g., a xenograft animal model assay, for their activity in suppressing tumor growth in a mammal. The selected compounds can be further tested to verify their efficacy in treating cancer. For example, a compound can be administered to an animal (e.g., a mouse) having cancer and its therapeutic effect is then assessed. Based on the results, appropriate dosage ranges and administration routes can be investigated and determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference in their entirety.

Shown in Examples 1-20 below are the structures of 20 exemplary compounds of Formula (I) and how they were prepared. The analytical data for the compounds thus prepared are also set forth in Examples 1-20 and the procedures for testing these compounds are described in Examples 21-25 that follow.

Example 1: Synthesis of Compound 1

Compound 1 was prepared according to the synthetic methods described in Chen et al., *European Journal of Medicinal Chemistry*, 2015, 100, 151-161.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column is chromatography was performed with Merck Kieselgel 60, No. 9385, 230-400 mesh ASTM silica gel as the stationary phase. Proton CH) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

1-(5-Ethylisoxazol-3-yl)-3-(4-(2-((6-(4-(2-hydroxyethyl)piperazin-1-yl)-2-methylpyrimidin-4-yl)amino)thiazol-5-yl)phenyl)urea (HCl salt)

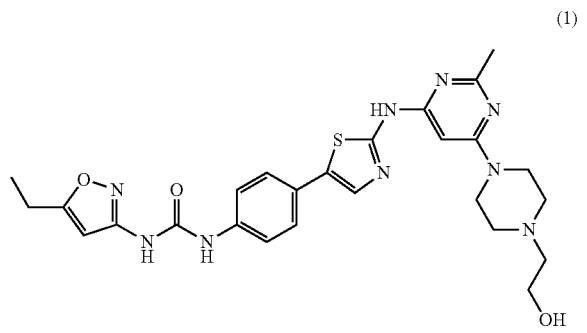 [SMILES: CCc1cc(NC(=O)Nc2ccc(-c3cnc(Nc4cc(N5CCN(CCO)CC5)nc(C)n4)s3)cc2)no1]

(1)

$^1$H NMR (400 MHz, DMSO-d6): δ 10.87 (s, 1H), 9.79 (s, 1H), 9.74 (s, 1H), 7.75 (s, 1H), 7.51 (q, J=8.8 Hz, 4H), 6.54 (s, 1H), 6.34 (s, 1H), 5.55 (br s, 1H), 4.37 (d, J=4.0 Hz, 2H), 3.78 (t, J=4.8 Hz, 2H), 3.61 (d, J=12.0 Hz, 2H), 3.48 (t, J=12.8 Hz, 2H), 3.19-3.12 (m, 4H), 2.69 (q, J=8.0 Hz, 2H), 2.47 (s, 3H), 1.19 (t, J=6.0 Hz, 3H); MS (ES$^+$) m/z calcd. for $C_{26}H_{3i}N_9O_3S$: 549.23. found: 550.3 (M+H$^+$).

In each of Examples 2-20 below, the compound was synthesized in the same manner as described in Example 1. Only the compound structure and analytical data are shown.

Example 2

1-(5-Ethylisoxazol-3-yl)-3-(4-(2-((6-(4-ethylpiperazin-1-yl)pyrimidin-4-yl)amino)thiazol-5-yl)phenyl)urea (HCl salt)

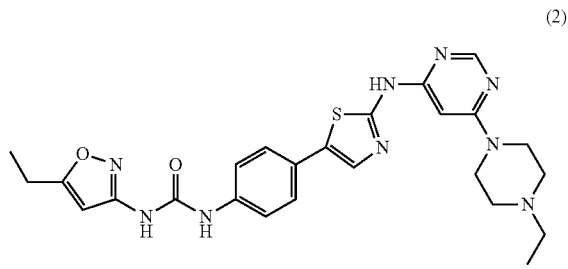 [SMILES: CCc1cc(NC(=O)Nc2ccc(-c3cnc(Nc4cc(N5CCN(CC)CC5)ncn4)s3)cc2)no1]

(2)

$^1$H NMR (400 MHz, DMSO-d6): δ 11.14 (s, 1H), 9.78 (s, 1H), 9.62 (s, 1H), 8.48 (s, 1H), 7.74 (s, 1H), 7.50 (q, J=8.8 Hz, 4H), 6.55 (s, 1H), 6.38 (s, 1H), 4.34 (d, J=14.0 Hz, 2H), 3.55 (d, J=11.6 Hz, 2H), 3.44-3.38 (m, 2H), 3.14-3.08 (m, 2H), 3.00 (q, J=9.6 Hz, 2H), 2.69 (q, J=7.6 Hz, 2H), 1.26 (t, J=7.6 Hz, 3H), 1.19 (t, J=7.6 Hz, 3H); MS (ES$^+$) m/z calcd. for $C_{25}H_{29}N_9O_2S$: 519.22. found: 520.2 (M+H$^+$).

Example 3

1-(5-Ethylisoxazol-3-yl)-3-(4-(2-((6-(2-morpholinoethoxy)pyrimidin-4-yl)amino)thiazol-5-yl)phenyl)urea (HCl salt)

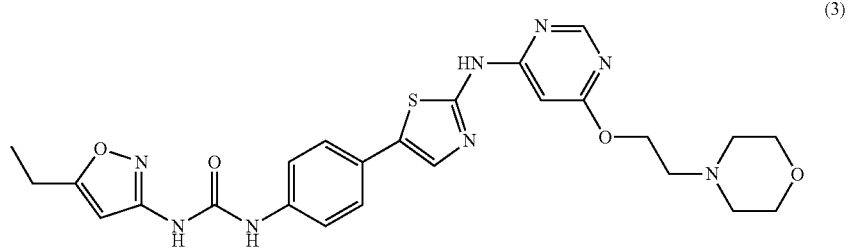 [SMILES: CCc1cc(NC(=O)Nc2ccc(-c3cnc(Nc4cc(OCCN5CCOCC5)ncn4)s3)cc2)no1]

(3)

$^1$H NMR (400 MHz, DMSO-d6): δ 11.08 (s, 1H), 9.75 (s, 1H), 9.56 (s, 1H), 8.62 (s, 1H), 7.73 (s, 1H), 7.50 (q, J=8.8 Hz, 4H), 6.54 (s, 1H), 6.50 (s, 1H), 4.71 (s, 2H), 3.95 (d, J=11.6 Hz, 2H), 3.79 (t, J=12.4 Hz, 2H), 3.56 (s, 2H), 3.47 (d, J=12.4 Hz, 2H), 3.15 (d, J=10.0 Hz, 2H), 2.69 (q, J=7.6 Hz, 2H), 1.19 (t, J=7.6 Hz, 3H); MS (ES$^+$) m/z calcd. for $C_{25}H_{28}N_8O_4S$: 536.20. found: 537.2 (M+H$^+$).

Example 4

1-(5-Ethylisoxazol-3-yl)-3-(4-(2-((6-(4-(2-hydroxyethyl)piperazin-1-yl)pyrimidin-4-yl)amino)thiazol-5-yl)phenyl)urea (HCl salt)

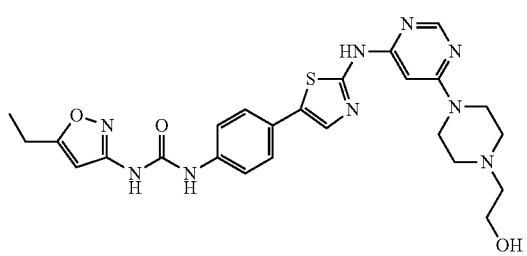

(4)

$^1$H NMR (300 MHz, DMSO-d6): δ 10.69 (s, 1H), 9.75 (s, 1H), 9.57 (s, 1H), 8.48 (s, 1H), 7.73 (s, 1H), 7.52 (s, 4H), 6.56 (s, 1H), 6.39 (s, 1H), 5.27 (br s, 1H), 4.34 (d, J=12.9 Hz, 2H), 3.80 (s, 2H), 3.62 (d, J=11.4 Hz, 2H), 3.44 (t, J=11.7 Hz, 2H), 3.22-312 (m, 4H), 2.71 (q, J=7.2 Hz, 2H), 1.21 (t, J=7.2 Hz, 3H); MS (ES$^+$) m/z calcd. for $C_{25}H_{29}N_9O_3S$: 535.21. found: 536.2 (M+H$^+$).

Example 5

1-(5-Ethylisoxazol-3-yl)-3-(4-(2-((6-(4-(2-fluoroethyl)piperazin-1-yl)pyrimidin-4-yl)amino)thiazol-5-yl)phenyl)urea (HCl salt)

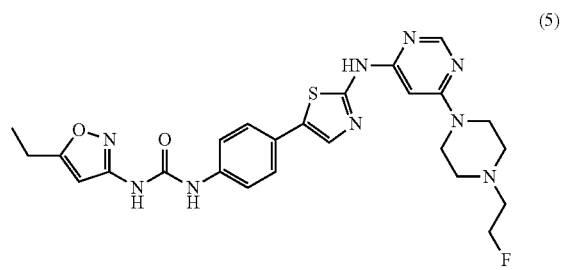 [SMILES: CCc1cc(NC(=O)Nc2ccc(-c3cnc(Nc4cc(N5CCN(CCF)CC5)ncn4)s3)cc2)no1]

(5)

$^1$H NMR (400 MHz, DMSO-d6): δ 11.56 (s, 1H), 9.78 (s, 1H), 9.62 (s, 1H), 8.48 (s, 1H), 7.74 (s, 1H), 7.52 (q, J=8.8 Hz, 4H), 6.56 (s, 1H), 6.39 (s, 1H), 4.99 (t, J=3.6 Hz, 1H), 4.88 (t, J=3.6 Hz, 1H), 4.38 (d, J=10.4 Hz, 2H), 3.59 (s, 2H), 3.44 (d, J=12.0 Hz, 4H), 3.19 (s, 2H), 2.71 (q, J=7.2 Hz, 2H), 1.21 (t, J=7.6 Hz, 3H); MS (ES$^+$) m/z calcd. for $C_{25}H_{28}FN_9O_2S$: 537.21. found: 538.2 (M+H$^+$).

Example 6

1-(5-Ethylisoxazol-3-yl)-3-(4-(2-((6-(4-(2-fluoroethyl)piperazin-1-yl)-2-methylpyrimidin-4-yl)amino)thiazol-5-yl)phenyl)urea (HCl salt)

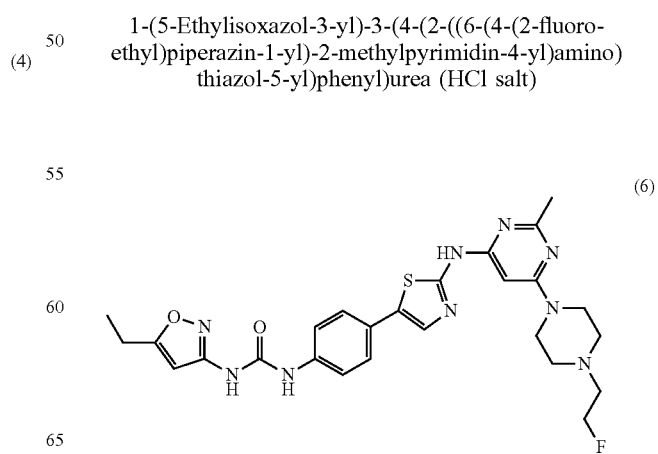

(6)

¹H NMR (300 MHz, DMSO-d6): δ 11.56 (s, 1H), 9.76 (s, 1H), 9.63 (s, 1H), 7.75 (s, 1H), 7.52 (t, J=13.2 Hz, 4H), 6.55 (s, 1H), 6.30 (s, 1H), 5.01 (s, 1H), 4.85 (s, 1H), 4.39 (s, 2H), 3.75-3.30 (m, 6H), 3.19 (s, 2H), 2.50 (s, 3H), 2.71 (q, J=7.2 Hz, 2H), 1.21 (t, J=7.5 Hz, 3H); MS (ES⁺) m/z calcd. for C₂₆H₃₀FN₉O₂S: 551.22. found: 552.2 (M+H⁺).

Example 7

1-(5-Ethylisoxazol-3-yl)-3-(2-fluoro-4-(2-((6-(4-(2-hydroxyethyl)piperazin-1-yl)-2-methylpyrimidin-4-yl)amino)thiazol-5-yl)phenyl)urea (freebase)

(7)

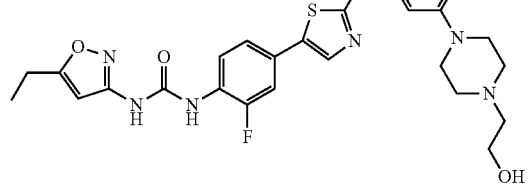

¹H NMR (400 MHz, DMSO-d6): δ 11.17 (s, 1H), 9.80 (s, 1H), 8.86 (s, 1H), 8.11 (t, J=8.6 Hz, 1H), 7.75 (s, 1H), 7.54 (d, J=12.8 Hz, 1H), 7.33 (d, J=8.8 Hz, 1H), 6.53 (s, 1H), 6.02 (s, 1H), 4.43 (t, J=5.4 Hz, 1H), 3.54-3.48 (m, 6H), 2.70 (q, J=8.2 Hz, 2H), 2.48-2.39 (m, 9H, overlapping with DMSO), 1.20 (t, J=8.2 Hz, 3H); MS (ES⁺) m/z Calcd. for C₂₆H₃₀FN₉O₃S: 567.22. found: 568.2 (M+H⁺).

Example 8

1-(5-(Tert-butyl)isoxazol-3-yl)-3-(4-(2-((6-(4-(2-hydroxyethyl)piperazin-1-yl)-2-methylpyrimidin-4-yl)amino)thiazol-5-yl)-2-methylphenyl)urea (freebase)

(8)

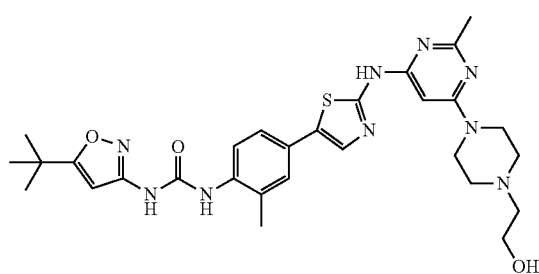

¹H NMR (400 MHz, DMSO-d6): δ 11.12 (s, 1H), 9.93 (s, 1H), 8.33 (s, 1H), 7.90 (d, J=8.8 Hz, 1H), 7.67 (s, 1H), 7.43 (s, 1H), 7.38 (d, J=8.8 Hz, 1H), 6.47 (s, 1H), 6.04 (s, 1H), 4.46 (s, 1H), 3.53-3.49 (m, 6H), 2.50-2.43 (m, 6H, overlapping with D-DMSO solvent peak), 2.42 (s, 3H), 2.28 (s, 3H), 1.30 (s, 9H); MS (ES⁺) m/z calcd. for C₂₉H₃₇N₉O₃S: 591.27. found: 592.3 (M+H⁺).

Example 9

1-(5-Ethylisoxazol-3-yl)-3-(4-(2-((6-(4-(2-hydroxyethyl)piperazin-1-yl)-2-methylpyrimidin-4-yl)amino)thiazol-5-yl)-2-methylphenyl)urea (HCl salt)

(9)

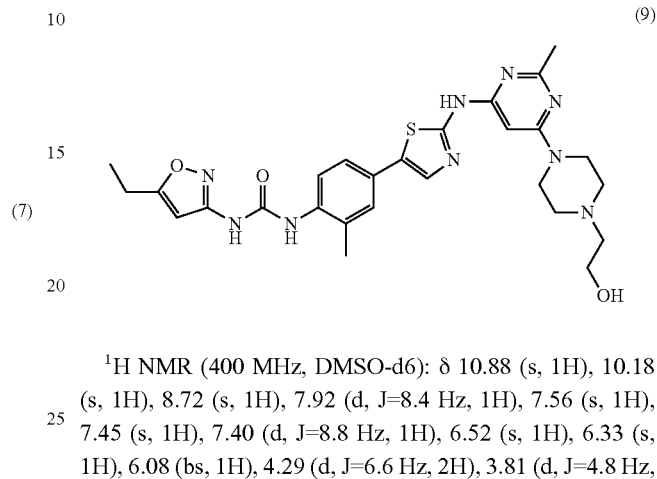

¹H NMR (400 MHz, DMSO-d6): δ 10.88 (s, 1H), 10.18 (s, 1H), 8.72 (s, 1H), 7.92 (d, J=8.4 Hz, 1H), 7.56 (s, 1H), 7.45 (s, 1H), 7.40 (d, J=8.8 Hz, 1H), 6.52 (s, 1H), 6.33 (s, 1H), 6.08 (bs, 1H), 4.29 (d, J=6.6 Hz, 2H), 3.81 (d, J=4.8 Hz, 2H), 3.64-3.61 (m, 2H), 3.51-3.41 (m, 2H), 3.22 (s, 2H), 3.16-3.13 (m, 2H), 2.71 (q, J=7.4 Hz, 2H), 2.54 (s, 3H), 2.31 (m, 3H), 1.21 (t, J=7.6 Hz, 3H); MS (ES⁺) m/z calcd. for C₂₇H₃₃N₉O₃S: 563.24. found: 564.2 (M+H⁺).

Example 10

1-(5-Cyclopropylisoxazol-3-yl)-3-(4-(2-((6-(4-(2-hydroxyethyl)piperazin-1-yl)-2-methylpyrimidin-4-yl)amino)thiazol-5-yl)-2-methylphenyl)urea (HCl salt)

(10)

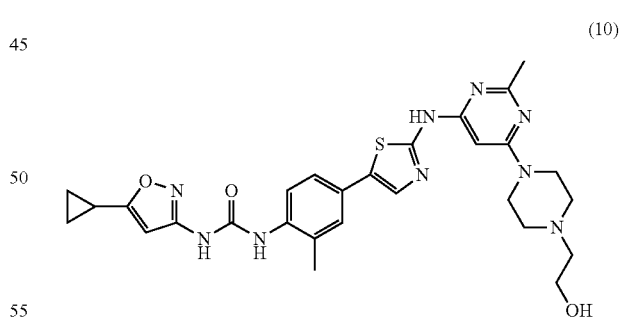

¹H NMR (400 MHz, DMSO-d6): δ 11.01 (s, 1H), 10.21 (s, 1H), 8.78 (s, 1H), 7.92 (d, J=8.8 Hz, 1H), 7.78 (s, 1H), 7.45 (s, 1H), 7.40 (d, J=8.4 Hz, 1H), 6.45 (s, 1H), 6.38 (s, 1H), 6.18 (bs, 1H), 4.38 (bs, 2H), 3.82 (d, J=5.0 Hz, 2H), 3.64 (d, J=5.6 Hz, 2H), 3.52 (t, J=6.1 Hz, 2H), 3.22 (m, 2H), 3.16-3.13 (m, 2H), 2.53 (s, 3H), 2.30 (s, 3H), 2.13-2.07 (m, 1H), 1.07-1.01 (m, 2H), 0.89-0.86 (m, 2H); MS (ES⁺) m/z calcd. for C₂₈H₃₃N₉O₃S: 575.24. found: 576.3 (M+H⁺).

Example 11

1-(5-Cyclopropylisoxazol-3-yl)-3-(2-fluoro-4-(2-((6-(4-(2-hydroxyethyl)piperazin-1-yl)-2-methylpyrimidin-4-yl)amino)thiazol-5-yl)phenyl)urea (HCl salt)

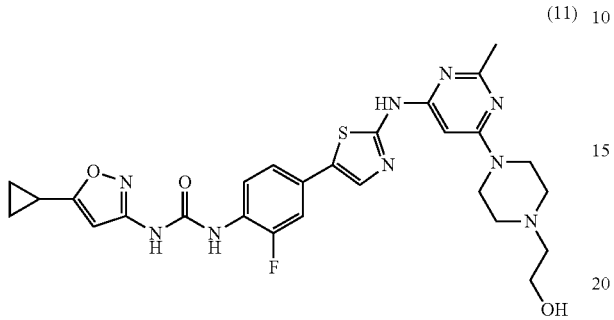

(11)

$^1$H NMR (400 MHz, DMSO-d6): δ 11.16 (s, 1H), 10.16 (s, 1H), 9.23 (s, 1H), 8.09 (t, J=8.4 Hz, 1H), 7.82 (s, 1H), 7.55 (d, J=12.4 Hz, 1H), 7.34 (d, J=8.4 Hz, 1H), 6.45 (s, 1H), 6.28 (s, 1H), 4.33 (bs, 2H), 3.80 (t, J=4.8 Hz, 2H), 3.60 (d, J=11.6 Hz, 2H), 3.49-3.40 (m, 2H), 3.19-3.11 (m, 4H), 2.35 (s, 3H), 2.10-2.06 (m, 1H), 1.04-0.99 (m, 2H), 0.88-0.84 (m, 2H); MS (ES$^+$) m/z Calcd. for $C_{27}H_{30}FN_9O_3S$: 579.22. found: 580.2 (M+H$^+$).

Example 12

1-(5-Ethylisoxazol-3-yl)-3-(4-(2-((6-(4-(2-hydroxyethyl)piperazin-1-yl)-2-(methylthio)pyrimidin-4-yl)amino)thiazol-5-yl)phenyl)urea (HCl salt)

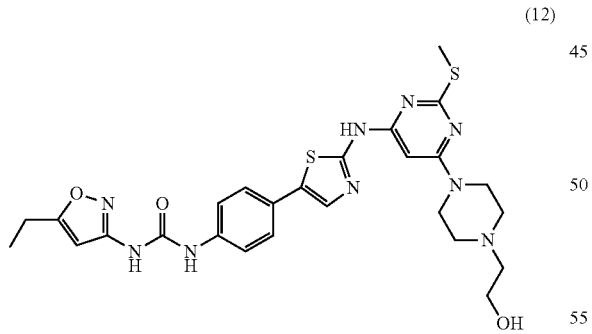

(12)

$^1$H NMR (400 MHz, DMSO-d6): δ 10.66 (s, 1H), 9.74 (s, 1H), 9.58 (s, 1H), 7.71 (s, 1H), 7.52-7.50 (s, 3H), 6.56 (s, 2H), 6.06 (s, 1H), 4.27 (d, J=6.0 Hz, 2H), 3.79 (t, J=5.0 Hz, 2H), 3.60 (d, J=6.0 Hz, 2H), 3.58 (t, J=6.0 Hz, 2H), 3.22-3.08 (m, 4H), 2.71 (q, J=7.6 Hz, 2H), 2.61 (s, 3H), 2.51 (s, 3H, overlapping with DMSO), 1.18-1.23 (m, 3H); MS (ES$^+$) m/z Calcd. for $C_{26}H_{33}Cl_2N_9O_3S_2$: 581.20. found: 582.2 (M+H$^+$).

Example 13

1-(5-Ethylisoxazol-3-yl)-3-(2-fluoro-4-(2-((6-(4-(2-hydroxyethyl)piperazin-1-yl)-2-(methylthio)pyrimidin-4-yl)amino)thiazol-5-yl)phenyl)urea (HCl salt)

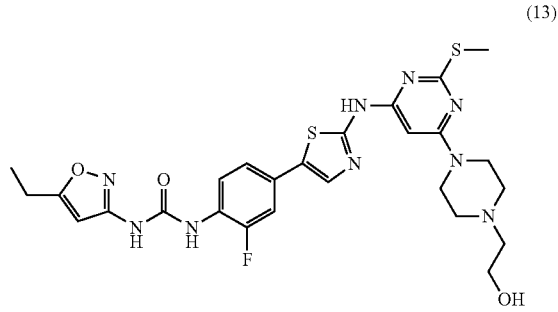

(13)

$^1$H NMR (300 MHz, DMSO-d6): δ 11.45 (s, 1H), 10.58 (s, 1H), 9.97 (s, 1H), 9.03 (s, 1H), 8.11 (t, J=8.6 Hz, 1H), 7.78 (s, 1H), 7.51 (d, J=12.9 Hz, 1H), 7.29 (d, J=9.0 Hz, 1H), 6.52 (s, 1H), 6.03 (s, 1H), 4.26 (d, J=12.6 Hz, 2H), 3.77 (d, J=4.8 Hz, 2H), 3.58 (d, J=11.4 Hz, 2H), 3.38 (t, J=12.3 Hz, 2H), 3.20-3.08 (m, 4H), 2.70 (q, J=7.6 Hz, 2H), 2.6 (s, 3H), 1.19 (t, J=7.5 Hz, 3H); MS (ES$^+$) m/z Calcd. for $C_{26}H_{30}FN_9O_3S_2$: 599.19. found: 600.3 (M+H$^+$).

Example 14

1-(5-Ethylisoxazol-3-yl)-3-(4-(2-((6-(4-(2-hydroxyethyl)piperazin-1-yl)-2-(methylthio)pyrimidin-4-yl)amino)thiazol-5-yl)-2-methylphenyl)urea (HCl salt)

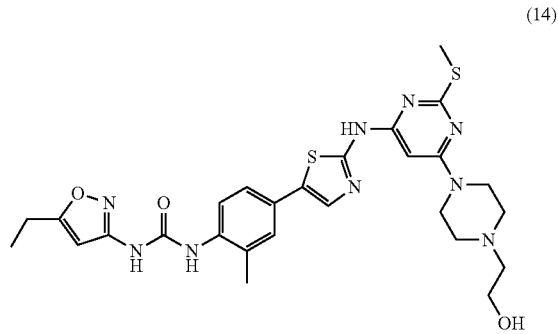 [SMILES: CCc1cc(NC(=O)Nc2ccc(-c3cnc(Nc4cc(N5CCN(CCO)CC5)nc(SC)n4)s3)cc2)no1]

(14)

$^1$H NMR (400 MHz, DMSO-d6): δ 10.72 (s, 1H), 10.12 (s, 1H), 8.66 (s, 1H), 7.90 (d, J=8.4 Hz, 1H), 7.71 (s, 1H), 7.41 (s, 1H), 7.35 (d, J=8.4 Hz, 1H), 6.51 (s, 1H), 6.07 (s, 1H), 5.96 (bs, 1H), 4.28 (d, J=6.6 Hz, 2H), 3.80 (d, J=5.0 Hz, 2H), 3.60 (d, J=5.8 Hz, 2H), 3.46-3.38 (m, 2H), 3.21-3.20 (m, 2H), 3.16-3.10 (m, 2H), 2.71 (q, J=7.5 Hz, 2H), 2.61 (s, 3H), 2.30 (s, 3H), 1.21 (t, J=7.6 Hz, 3H); MS (ES$^+$) m/z calcd, for $C_{27}H_{33}N_9O_3S_2$: 595.21. found: 596.3 (M+H$^+$).

Example 15

1-(4-(2-((6-(3-(Dimethylamino)pyrrolidin-1-yl)-2-methylpyrimidin-4-yl)amino)thiazol-5-yl)-2-methyl-phenyl)-3-(5-ethylisoxazol-3-yl)urea (HCl salt)

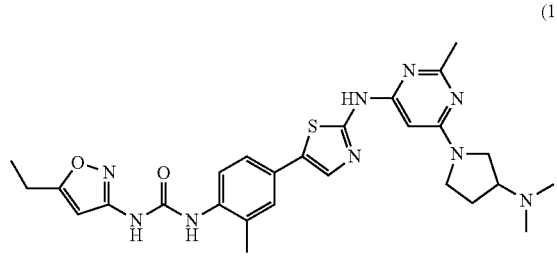

(15)

$^1$H NMR (400 MHz, DMSO-d6): δ 11.70 (s, 1H), 10.22 (s, 1H), 8.75 (s, 1H), 7.93 (d, J=8.8 Hz, 1H), 7.78 (s, 1H), 7.45 (s, 1H), 7.39 (d, J=8.8 Hz, 1H), 6.52 (s, 1H), 6.16 (s, 1H), 4.02 (s, 2H), 3.89 (s, 1H), 3.75 (s, 1H), 3.48 (s, 1H), 2.80 (s, 6H), 2.71 (q, J=7.2 Hz, 2H), 2.59 (s, 3H), 2.44-2.39 (m, 2H), 1.07-1.03 (m, 3H); MS (ES$^+$) m/z Calcd. for $C_{27}H_{33}N_9O_2S$: 547.25. found: 548.2 (M+H$^+$).

Example 16

1-(4-(2-((6-(3-(Dimethylamino)pyrrolidin-1-yl)-2-methylpyrimidin-4-yl)amino)thiazol-5-yl)-2-fluoro-phenyl)-3-(5-ethylisoxazol-3-yl)urea (HCl salt)

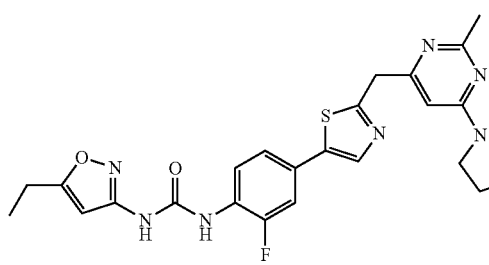

(16)

$^1$H NMR (400 MHz, DMSO-d6): δ 11.78 (s, 1H), 10.16 (s, 1H), 9.21 (s, 1H), 8.11 (t, J=8.8 Hz, 1H), 7.86 (s, 1H), 7.57 (d, J=12.0 Hz, 1H), 7.34 (d, J=8.0 Hz, 1H), 6.52 (s, 1H), 6.17 (s, 1H), 4.10-3.76 (m, 4H), 3.49 (bs, 1H), 2.78 (s, 6H), 2.69 (q, J=7.6 Hz, 2H), 2.61 (s, 3H), 1.19 (t, J=7.6 Hz, 3H); MS (ES$^+$) m/z calcd. for $C_{26}H_{30}FN_9O_2S$: 551.22. found: 552.2 (M+H$^+$).

Example 17

1-(4-(2-((6-(3-(Dimethylamino)pyrrolidin-1-yl)-2-methylpyrimidin-4-yl)amino)thiazol-5-yl)phenyl)-3-(5-ethylisoxazol-3-yl)urea (HCl salt)

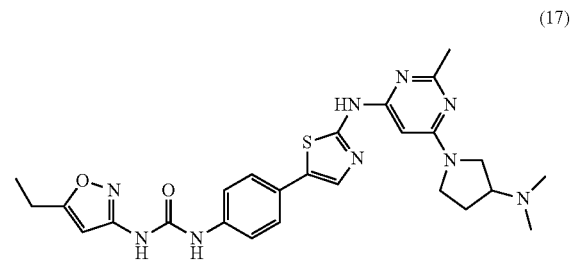 [SMILES: CCc1cc(NC(=O)Nc2ccc(-c3cnc(Nc4cc(N5CCC(N(C)C)C5)nc(C)n4)s3)cc2)no1]

(17)

$^1$H NMR (400 MHz, DMSO-d6): δ 11.73 (s, 1H), 9.85 (s, 1H), 9.84 (s, 1H), 7.79 (s, 1H), 7.55-7.47 (m, 4H), 6.56 (s, 1H), 6.19 (s, 1H), 4.03 (d, J=6.4 Hz, 2H), 3.93 (s, 1H), 3.77 (s, 1H), 3.50 (s, 1H), 2.81 (s, 6H), 2.61 (s, 3H), 2.80-2.68 (m, 2H), 2.43 (q, J=8.4 Hz, 2H), 1.21 (t, J=7.6 Hz, 3H); MS (ES$^+$) m/z Calcd. for $C_{26}H_{31}N_9O_2S$: 533.23. found: 534.2 (M+H$^+$).

Example 18

1-(4-(2-((6-(4-(Dimethylamino)piperidin-1-yl)-2-methylpyrimidin-4-yl)amino)thiazol-5-yl)-2-methyl-phenyl)-3-(5-ethylisoxazol-3-yl)urea (HCl salt)

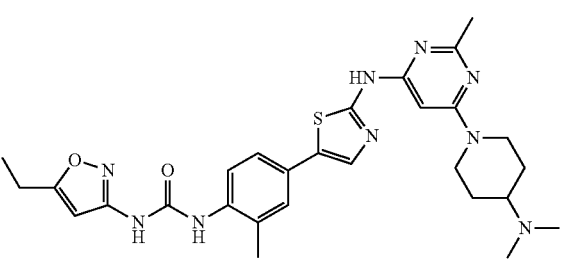

(18)

$^1$H NMR (400 MHz, DMSO-d6): δ 11.10 (s, 1H), 10.23 (s, 1H), 8.77 (s, 1H), 7.92 (d, J=8.4 Hz, 1H), 7.78 (s, 1H), 7.45 (s, 1H), 7.40 (d, J=6.4 Hz, 1H), 6.52 (s, 1H), 6.44 (s, 1H), 4.44 (s, 2H), 3.46 (bs, 1H), 3.05 (t, J=12.0 Hz, 2H), 2.74-2.68 (m, 8H), 2.55 (s, 3H), 2.31 (s, 3H), 2.46 (d, J=10.8 Hz, 2H), 2.66 (q, J=11.6 Hz, 2H), 1.20 (t, J=7.6 Hz, 3H); MS (ES$^+$) m/z Calcd. for $C_{28}H_{35}N_9O_2S$: 561.26. found: 562.2 (M+H$^+$).

Example 19

1-(4-(2-((6-(4-(Dimethylamino)piperidin-1-yl)-2-methylpyrimidin-4-yl)amino)thiazol-5-yl)phenyl)-3-(5-ethylisoxazol-3-yl)urea (HCl salt)

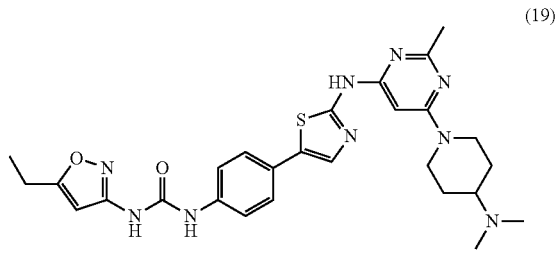 [SMILES: CCc1cc(NC(=O)Nc2ccc(-c3cnc(Nc4cc(N5CCC(N(C)C)CC5)nc(C)n4)s3)cc2)no1]

(19)

$^1$H NMR (300 MHz, DMSO-d6): δ 10.98 (s, 1H), 9.78 (s, 1H), 9.72 (s, 1H), 7.76 (s, 1H), 7.55-7.48 (m, 4H), 6.54 (s, 1H), 6.40 (s, 1H), 4.42 (bs, 2H), 3.43 (t, J=6.8 Hz, 1H), 3.02 (t, J=12.3 Hz, 2H), 2.73-2.66 (m, 8H), 2.52-2.48 (m, 3H, overlapping with DMSO), 2.16 (t, J=10.8 Hz, 2H), 1.64 (q, J=11.1 Hz, 2H), 1.22-1.17 (m, 3H); MS (ES$^+$) m/z Calcd. for $C_{27}H_{33}N_9O_2S$: 547.25. found: 548.2 (M+H$^+$).

Example 20

1-(4-(2-((6-(4-(Dimethylamino)piperidin-1-yl)-2-methylpyrimidin-4-yl)amino)thiazol-5-yl)-2-fluorophenyl)-3-(5-ethylisoxazol-3-yl)urea (HCl salt)

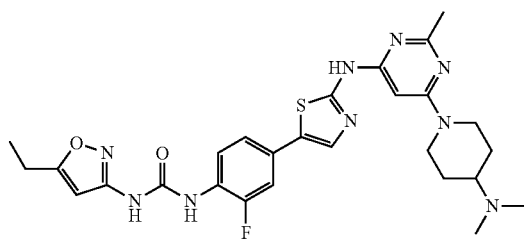

(20)

$^1$H NMR (400 MHz, DMSO-d6): δ 10.78 (s, 1H), 9.98 (s, 1H), 9.05 (s, 1H), 8.11 (t, J=8.8 Hz, 1H), 7.82 (s, 1H), 7.57 (d, J=12.4 Hz, 1H), 7.34 (d, J=8.8 Hz, 1H), 6.52 (s, 1H), 6.26 (s, 1H), 4.39 (bs, 2H), 3.41 (t, J=6.8 Hz, 1H), 2.95 (t, J=11.2 Hz, 2H), 2.74-2.68 (m, 8H), 2.52-2.47 (m, 3H, overlapping with DMSO), 2.13 (d, J=10.8 Hz, 2H), 1.60 (q, J=12.0 Hz, 2H), 1.19 (t, J=7.6 Hz, 3H); MS (ES$^+$) m/z Calcd. for $C_{27}H_{32}FN_9O_2S$: 565.24. found: 566.2 (M+H$^+$).

Example 21: Inhibition of Protein Kinase

Kinase inhibition data were obtained from SelectScreen® Biochemical Kinase Profiling Service.

More specifically, test compounds were screened in 160 nL of a 1% DMSO solution in the well of a 384-well plate; kinase/antibody mixtures (8 μL) were diluted to a 2-fold working concentration in an appropriate kinase buffer (3.84 μL) and a 4-fold AlexaFluor® labeled tracer (4 μL) was prepared in the kinase buffer; incubation of test solutions was conducted at room is temperature for 60 minutes; and readout on a fluorescence plate reader was recorded and analyzed.

TABLE 1

| | Kinase inhibition data | | |
|---|---|---|---|
| | Inhibition (% of control) at 100 nM | | |
| Protein Kinases | 1 | 2 | 3 |
| ABL1 | 81 | — | — |
| ABL1 T315I | 65 | — | 15 |
| DDR1 | — | 80 | 77 |
| KIT | 66 (41 nM)* | 67 | 85 |
| PDGFR A | 95 (9 nM)* | 89 | 79 |
| PDGFR B | 82 (19 nM)* | 80 | 92 |
| RET | 96 | 94 | 56 |
| SRC | 96 (6 nM)* | 79 | 66 |
| TRK A | — | 60 | 69 |
| TRK B | — | 72 | 73 |
| VEGFR2 | 95 (19 nM)* | — | — |

*The number in the bracket indicates a IC$_{50}$ value.

It was observed that certain compounds of Formula (I), e.g., Compounds 1, 2, and 3, unexpectedly inhibited multiple protein kinases with half maximal inhibitory concentrations or IC$_{50}$ values lower than 100 nM.

The results indicate that compounds of Formula (I) exert high activities in inhibiting multiple protein kinases.

Example 22: In Vitro Cellular Activity

AC220 is a small molecule FLT3 inhibitor in clinical trials, which exerts high potency against FLT3-internal tandem duplication (FLT3-ITD) mutant. Clinically relevant AC220 resistance-conferring mutations have been restricted to residues in the FLT3 kinase domain, e.g., ITD-D835Y, ITD-D835V, ITD-D835F, ITD-F691L, and ITD-F691I.

A study was performed to assess the potency of compounds of Formula (I) in inhibiting growth of cell lines containing these mutants, compared with that of compound AC220, as is follows.

The five leukemic 32D cell lines were purchased from American Type Culture Collection (ATCC, Manassas, Va., USA). Murine pro-B lymphocyte 32D cell lines were stably transfected with expression vectors that encoded human FLT3 containing an ITD mutation (32D-ITD cells), ITD and D835Y (32D-ITD/D835Y cells), ITD and D835V (32D-ITD/D835V cells), ITD and D835F (32D-ITD/D835F cells), and ITD and F691L (32D-ITD/F691L cells) mutations, which lead to constitutive activation of the FLT3 downstream signaling proteins. The cell viability was assessed with the MTS assay described in PLoS One, 2014, 9, e97116. 32D-ITD/D835Y, 32D-ITD/D835V, 32D-ITD/D835F, 32D-ITD/F691L, and 32D-ITD/F691I cells were seeded in 96-well plates at 1×10$^4$ cells/mL (100 μL per well) for 24-h incubation. Test compounds (at various concentrations in dimethyl sulfoxide (DMSO) were subsequently added to the culture medium for 72-h incubation. The cell viability was determined by the MTS assay (Promega, Madison, Wis., USA).

Results shown in Table 2 below were obtained from the study of test compounds in inhibiting growth of cell lines containing ITD mutants

TABLE 2

Activity of compounds against 32D cells expressing AC220-resistant mutants of FLT3-ITD

| $GI_{50}$ (nM) | AC220 | 1 | 2 | 4 |
|---|---|---|---|---|
| ITD-D835Y | 19 | 1.1 | 1.8 | 1.0 |
| ITD-D835V | 103 | 0.76 | 1.5 | 0.87 |
| ITD-D835F | 57 | 3.2 | 5.8 | 5.5 |
| ITD-F691L | 101 | 8.5 | 14 | 12 |
| ITD-F691I | >300 | 45 | 158 | 19 |

It was observed that compounds 1, 2, and 4 all unexpectedly exhibited much higher cell growth inhibitory effects than those exerted by AC220 against all mutants ITD-D835Y, ITD-D835V, ITD-D835F, ITD-F691L, and ITD-F691I. More specifically, all Compounds 1, 2, and 4 unexpectedly exerted high cell growth inhibitory effects with $GI_{50}$ values lower than 6 nM against mutants ITD-D835Y, ITD-D835V, and ITD-D835F, compared with $GI_{50}$ values of 19-103 nM exerted by AC220; and Compound 4 unexpectedly exerted high cell growth inhibitory effects with $GI_{50}$ values lower than 20 nM against mutants ITD-F691L and ITD-F691I, compared with $GI_{50}$ values higher than 100 nM exerted by AC220.

The comparative data indicate that compounds of Formula (I) unexpectedly exert high cellular potency and outperforms a clinical compound in inhibiting certain protein kinase mutants.

Example 23: Oral Bioavailability (F %) of Compounds of Formula (I)

A study was performed to evaluate in vivo exposures of compounds of formula (I) when administered orally as follows.

Male ICR mice weighing 25-35 g each were obtained from BioLASCO (Taiwan Co., Ltd, Ilan, Taiwan). The animal studies were performed according to the National Health Research Institutes (NHRI) institutional animal care and committee-approved procedures. A single dose at 2.0 mg/kg of each of Compounds 2, 3, 5, and 6 was administered intravenously (IV) to a total of 33 male mice. A single dose at 10 mg/kg of each of these four compounds was administered orally (PO) to a total of 27 male mice. Each mouse was given 100 mL of the IV dosing solution by intravenous tail-vein injection and 200 mL of the PO dosing solution by oral gavage. Animals that received the IV dose were not fasted and that received the PO dose were fasted overnight prior to dosing. At 0 (immediately before dosing), 2 (IV only), 5 (IV only), 15 and 30 min and at 1, 2, 4, 6, 8, 16 and 24 h after dosing, blood (~500 mL) was collected from groups of 3 mice at each time point by cardio puncture and stored in ice (0-4° C.). Ethylenediaminetetraacetic acid (EDTA) was used as the anticoagulant. Plasma was separated from the blood by centrifugation (3000 rpm for 15 minutes at 4° C. in a Beckman Model Allegra 6R centrifuge) and stored in a freezer (−20° C.). Control plasma was obtained from mice receiving no compound for use of constructing the standard curve and for the preparation of quality control (QC) samples. All samples were analyzed for the parent compound by LC-MS/MS.

Oral bioavailability, presented as a percentage (F %), was calculated from dividing the average area under the curve (AUC) value of a compound after PO dosing by the average AUC value of the compound after IV dosing following dose normalization. Values of AUC and F % are shown in Table 3 below.

TABLE 3

Pharmacokinetic profiles of compounds of Formula (I) in mice

| Compounds | IV (dose: 2 mg/kg) $AUC_{(0-inf)}$ (ng/mL*hr) | PO (dose: 10 mg/kg) $AUC_{(0-inf)}$ (ng/mL*hr) | F (%) |
|---|---|---|---|
| 2 | 1441 | 2796 | 38 |
| 3 | 2074 | 11371 | 96 |
| 5 | 2725 | 8239 | 67 |
| 6 | 1837 | 7583 | 89 |

It was observed that all four Compounds, i.e., 2, 3, 5, and 6, unexpectedly exerted high exposures as indicated by both IV AUC and PO AUC values. Also, Compounds 2, 3, 5, and 6 unexpectedly exhibited high oral bioavailability with F % values of 38, 96, 67, and 89, respectively.

The results set forth in Table 3 above indicate that compounds of Formula (I) unexpectedly exhibit high in vivo exposure when administered orally.

Example 24: Efficacy in Xenograft Mouse Models

A study was performed to evaluate in vivo efficacy of compounds of formula (I), i.e., tumor growth inhibition (TGI), as follows.

Male nude mice (Nu-Fox1$^{nu}$) of 8 weeks old were purchased from BioLASCO (Taipei, Taiwan, R.O.C.). Human colorectal Colo205, pancreatic Mia-PaCa 2 tumor cells or MOLM-13, 32D-ITD/D835Y leukemia cells were inoculated subcutaneously at 1×10$^6$ cells each in the nude mice. All human cancer cells were detected as free of *Mycoplasma* spp before they were injected into animals. The tumor cells grow as xenograft tumors and the tumor size reached approximately 200-250 mm$^3$ in the nude mice ready for dose treatments. Test compounds were dissolved in 20% 2-hydroxypropy-β-cyclodextrin individually for oral gavage administrations to the nude mice. The tumor-bearing mice were treated with test compounds at various doses, 5 times a week for 2 weeks. Tumor sizes were measured by an electronic caliper and calculated with the formula: tumor size=length×width$^2$/2. Tumor size and animal body weight were measured twice a week before and after the tumor cell inoculation throughout the observation period. Uses of animals and experimental procedures thereof were approved by the Institutional Animal Care and Use Committee (IACUC) of the National Health Research Institutes.

TABLE 4

In vivo efficacy of compounds of Formula (I) against xenografts colo205 model in nude mice

| Colo205 xenografts in nude mice | Day 18 TGI |
|---|---|
| 1 | >80% |
| 2 | ~80% |
| 3 | ~80% |
| 4 | ~80% |
| 6 | ~80% |

As shown in Table 4 above, in the xenograft colo205 model in nude mice, all of the test compounds, i.e., Compounds 1 (PO; 50 mg/kg), 2 (PO; 50 mg/kg), 3 (PO; 100 mg/kg), 4 (PO; 150 mg/kg), and 6 (PO; 25 mg/kg), unexpectedly exerted high TGI with a value of 80% at day 18.

TABLE 5

In vivo antitumor efficacy of compounds of Formula
(I) against xenograft Mia-paca2 tumor model

| Mia-paca2 tumor model | Day 18 TGI |
|---|---|
| 5 | 65% |
| 6 | 68% |

As shown in Table 5 above, in the xenograft Mia-paca2 tumor model, both compounds 5 and 6, orally administered at 25 mg/kg, unexpectedly exerted high TGI with respective values of 65% and 68% at day 18.

TABLE 6

In vivo efficacy of compounds of Formula (I)
against xenografts MOLM-13 model in nude mice

| MOLM-13 xenografts in nude mice | Day 25 tumor size |
|---|---|
| 2 | 53 mm$^3$ (50 mpk), 270 mm$^3$ (25 mpk) |
| 4 | 193 mm$^3$ (150 mpk) |

*Starting tumor size ~250 mm$^3$. At day 18, tumor size of control reached to >2000 mm$^3$ and mice were sacrificed.

As shown in Table 6 above, in the xenograft MOLM-13 model in nude mice, both compounds 2 (PO; 25 and 50 mg/kg) and 4 (PO; 150 mg/kg) unexpectedly exerted high TGI and is tumor regression at day 25.

TABLE 7

In vivo efficacy of compounds of Formula (I) against
xenografts FLT3-ITD-D835Y model in nude mice

| MOLM-13 xenografts in nude mice | Day 12 tumor regression |
|---|---|
| 2 | 34% |
| 5 | 22% |

As shown in Table 7 above, in the xenograft FLT3-ITD-D835Y model in nude mice, both compounds 2 (PO; 25 mg/kg) and 5 (PO; 25 mg/kg) unexpectedly exerted high tumor regression with a value of >20% at day 12.

These results indicate that compounds of Formula (I), when administered orally, unexpectedly exert high antitumor efficacy in xenograft animal models.

Example 25: Toxicity Studies in Mice

A study was performed to evaluate in vivo toxicity of compounds of formula (I) as follows.

Compounds of formula (I) were tested in animals for their in vivo efficacy following the procedure described in EXAMPLE 24. Nine weeks old athymic nu/nu nude mice were administered orally at a once daily dose of 25, 50, 100, or 150 mg/kg on days 1-5 and 8-12. The mice were observed for clinical signs and measured for body weights during the 14-day post-treatment observation period.

TABLE 8

In vivo toxicity study of compounds of Formula
(I) in xenografts colo205 nude mice

| Compounds | Toxicity: 5 on 2 off × 2 Mortality (nude mice n = 6) |
|---|---|
| 1 | 0/6 (50 mg/kg) |
| 2 | 0/6 (50 mg/kg) |
| 3 | 0/6 (100 mg/kg) |
| 4 | 0/6 (150 mg/kg) |
| 6 | 0/6 (25 mg/kg) |

As shown in Table 8 above, xenografts colo205 nude mice well tolerated. Compounds 1, 2, 3, 4, and 6, which were administered orally (50, 50, 100, 150 and 25 mg/kg) once daily. No mortality was observed during the study.

TABLE 9

In vivo toxicity study of compounds of Formula
(I) in xenografts Mia-paca2 nude mice

| Mia-paca2 tumor model | Toxicity: 5 on 2 off × 2 Mortality (nude mice n = 6) |
|---|---|
| 5 | 0/6 (25 mg/kg) |
| 6 | 0/6 (25 mg/kg) |

As shown in Table 9 above, xenografts Mia-paca2 nude mice well tolerated. Compounds 5 and 6, which were administered orally (25 mg/kg) once daily. Again, no mortality was observed during this study.

TABLE 10

In vivo toxicity study of compounds of Formula
(I) in xenografts MOLM-13 nude mice

| Compounds | Toxicity: 5 on 2 off × 2 Mortality (nude mice n = 6 or 7) |
|---|---|
| 2 | 0/6 (25 or 50 mg/kg) |
| 4 | 0/6 (150 mg/kg) |

As shown in Table 10 above, xenografts MOLM-13 nude mice well tolerated. Compounds 2 and 4, which were administered orally (25 and 50, 50 or 150 mg/kg) once daily. No mortality was observed during this study as well.

TABLE 11

In vivo toxicity study of compounds of Formula
(I) in xenografts FLT3-ITD-D835Y nude mice

| Compounds | Toxicity: 5 on 2 off × 2 Mortality (nude mice n = 8) |
|---|---|
| 2 | 0/8 (25 mg/kg) |
| 5 | 0/8 (25 mg/kg) |

As shown in Table 11 above, xenografts FLT3-ITD-D835Y nude mice well tolerated. Compounds 2 and 5, which were administered orally (25 mg/kg) once daily. No mortality was is observed during this study.

These results set forth above demonstrate that compounds of Formula (I) unexpectedly exhibit desirable safety profiles.

Other Embodiments

All of the features disclosed in this specification may be combined in any combination. Each feature disclosed in this specification may be replaced by an alternative feature

What is claimed is:

1. A compound of formula (I):

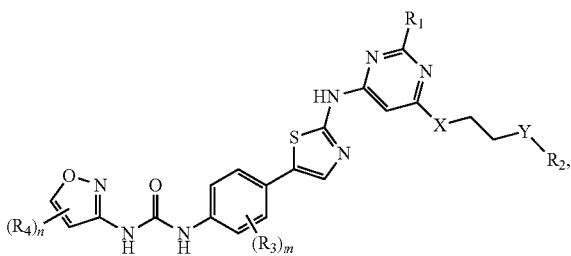

wherein
- $R_1$ is H;
- X is O or $NR_a$, $R_a$ being H or $C_{1-6}$ alkyl;
- Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl;
- $R_2$ is $CH_2CH_2R_e$ or $NR_fR_g$, in which $R_e$ is H, halo, or $OR_h$, each of $R_f$ and $R_g$, independently, being $C_{1-6}$ alkyl or $C_{3-8}$ cycloalkyl, and $R_h$ being H or $C_{1-6}$ alkyl, or $R_h$, together with $R_d$, the oxygen atom bonded to $R_h$, and the nitrogen atom bonded to $R_d$, being $C_{3-10}$ heterocycloalkyl;
- $R_3$ is H, halo, nitro, cyano, amino, $C_{1-6}$ alkyl, $C_{1-6}$ alkoxyl, $C_{3-10}$ cycloalkyl, $C_{3-10}$ heterocycloalkyl, aryl, or heteroaryl;
- $R_4$ is ethyl;
- m is 1, 2, 3, or 4; and
- n is 1 or 2.

2. The compound of claim 1, having formula (II):

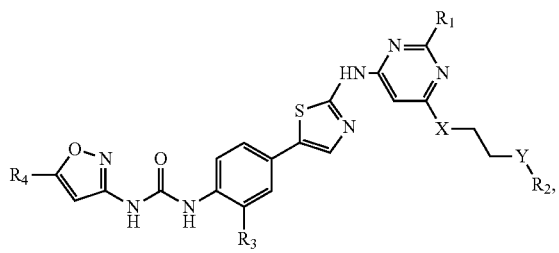

wherein X is O.

3. The compound of claim 2, wherein Y is $NR_d$ and $R_2$ is $-CH_2CH_2R_e$, in which $R_e$ is $OR_h$, $R_h$, together with $R_d$, the oxygen atom bonded to $R_h$, and the nitrogen atom bonded to $R_d$, being $C_{3-10}$ heterocycloalkyl; and $R_3$ is H, halo, or $C_{1-6}$ alkyl.

4. The compound of claim 3, wherein the compound is

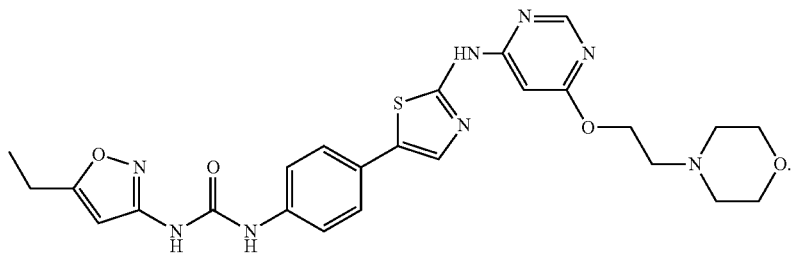 [SMILES: CCc1cc(NC(=O)Nc2ccc(-c3cnc(Nc4cc(OCCN5CCOCC5)ncn4)s3)cc2)no1]

5. The compound of claim 1, having formula (II):

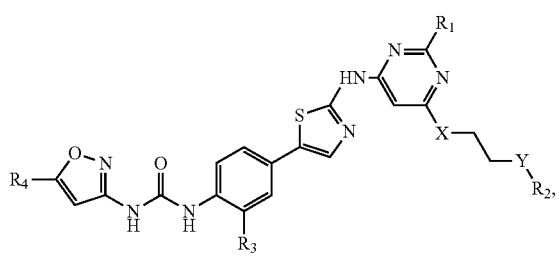

wherein X is $NR_a$, $R_a$ being H or $C_{1-6}$ alkyl.

6. The compound of claim 5, wherein
- Y is $CR_bR_c$, in which $R_b$, together with $R_a$, the carbon atom bonded to $R_b$, and the nitrogen atom bonded to $R_a$, is $C_{3-10}$ heterocycloalkyl, and $R_c$ is H, halo, $C_{1-6}$ alkyl, $C_{1-6}$ alkoxyl, or amino;
- $R_2$ is $NR_fR_g$, each of $R_f$ and $R_g$, independently, being $C_{1-6}$ alkyl or $C_{3-8}$ cycloalkyl; and
- $R_3$ is H, halo, $C_{1-6}$ alkyl, or $C_{3-10}$ cycloalkyl.

7. The compound of claim 6, wherein $R_b$, together with $R_a$, the carbon atom bonded to $R_b$, and the nitrogen atom bonded to $R_a$, is pyrrolidinyl or piperidinyl.

8. The compound of claim 5, wherein
Y is $NR_d$, in which $R_d$, together with $R_a$ and the nitrogen atoms bonded to $R_d$ and $R_a$, is $C_{3-10}$ heterocycloalkyl;
$R_2$ is —$CH_2CH_2R_e$, in which $R_e$ is H, halo, or $OR_h$, $R_h$ being H or $C_{1-6}$ alkyl; and
$R_3$ is H, halo, $C_{1-6}$ alkyl, or $C_{3-10}$ cycloalkyl.

9. The compound of claim 8, wherein $R_d$, together with $R_a$ and the nitrogen atoms bonded to $R_d$ and $R_a$, is piperazinyl.

10. The compound of claim 9, wherein the compound is

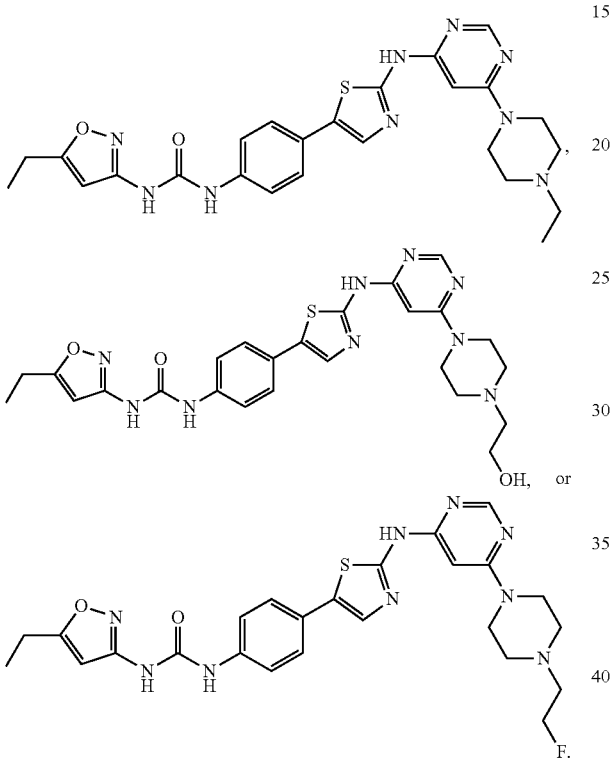

11. A compound of formula (I):

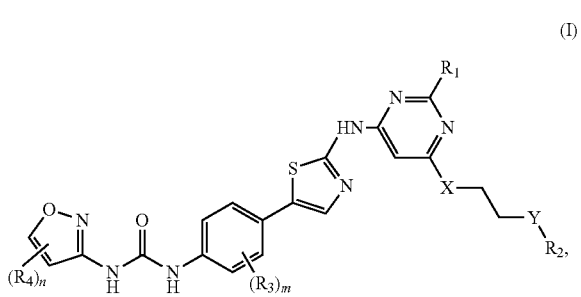

wherein
$R_1$ is $C_{1-6}$ alkyl or $C_{1-6}$ thioalkyl;
X is O or $NR_a$, $R_a$ being H or $C_{1-6}$ alkyl;
Y is $CR_bR_c$ or $NR_d$, in which each of $R_b$ and $R_c$, independently, is H, halo, $C_{1-6}$ alkyl, $C_{1-6}$ alkoxyl, or amino, and $R_d$ is H or $C_{1-6}$ alkyl; or $R_b$, together with $R_a$, the carbon atom bonded to $R_b$, and the nitrogen atom bonded to $R_a$, is $C_{3-10}$ heterocycloalkyl, or $R_d$, together with $R_a$ and the nitrogen atoms bonded to $R_d$ and $R_a$, is $C_{3-10}$ heterocycloalkyl;
$R_2$ is —$CH_2CH_2R_e$ or $NR_fR_g$, in which $R_e$ is halo, each of $R_f$ and $R_g$, independently, being $C_{1-6}$ alkyl or $C_{3-8}$ cycloalkyl, or $R_h$, together with $R_d$, the oxygen atom bonded to $R_h$, and the nitrogen atom bonded to $R_d$, being $C_{3-10}$ heterocycloalkyl;
$R_3$ is H, halo, nitro, cyano, amino, $C_{1-6}$ alkyl, $C_{1-6}$ alkoxyl, $C_{3-10}$ cycloalkyl, $C_{3-10}$ heterocycloalkyl, aryl, or heteroaryl;
$R_4$ is ethyl;
m is 1, 2, 3, or 4; and
n is 1 or 2.

12. The compound of claim 11, having formula (II):

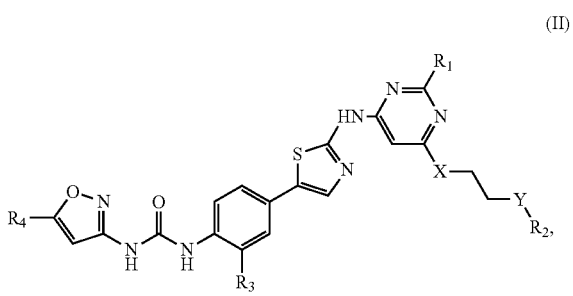

wherein X is O.

13. The compound of claim 11, having formula (II):

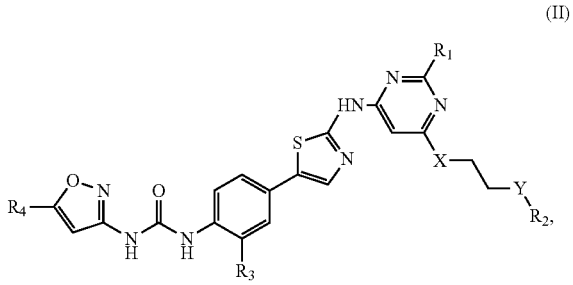

wherein X is $NR_a$, $R_a$ being H or $C_{1-6}$ alkyl.

14. The compound of claim 13, wherein
Y is $CR_bR_c$, in which $R_b$, together with $R_a$, the carbon atom bonded to $R_b$, and the nitrogen atom bonded to $R_a$, is $C_{3-10}$ heterocycloalkyl, and $R_c$ is H or $C_{1-6}$ alkyl;
$R_2$ is $NR_fR_g$, each of $R_f$ and $R_g$, independently, being $C_{1-6}$ alkyl or $C_{3-8}$ cycloalkyl; and
$R_3$ is H, halo, $C_{1-6}$ alkyl, or $C_{3-10}$ cycloalkyl.

15. The compound of claim 14, wherein $R_b$, together with $R_a$, the carbon atom bonded to $R_b$, and the nitrogen atom bonded to $R_a$, is pyrrolidinyl or piperidinyl.

16. The compound of claim 15, wherein the compound is

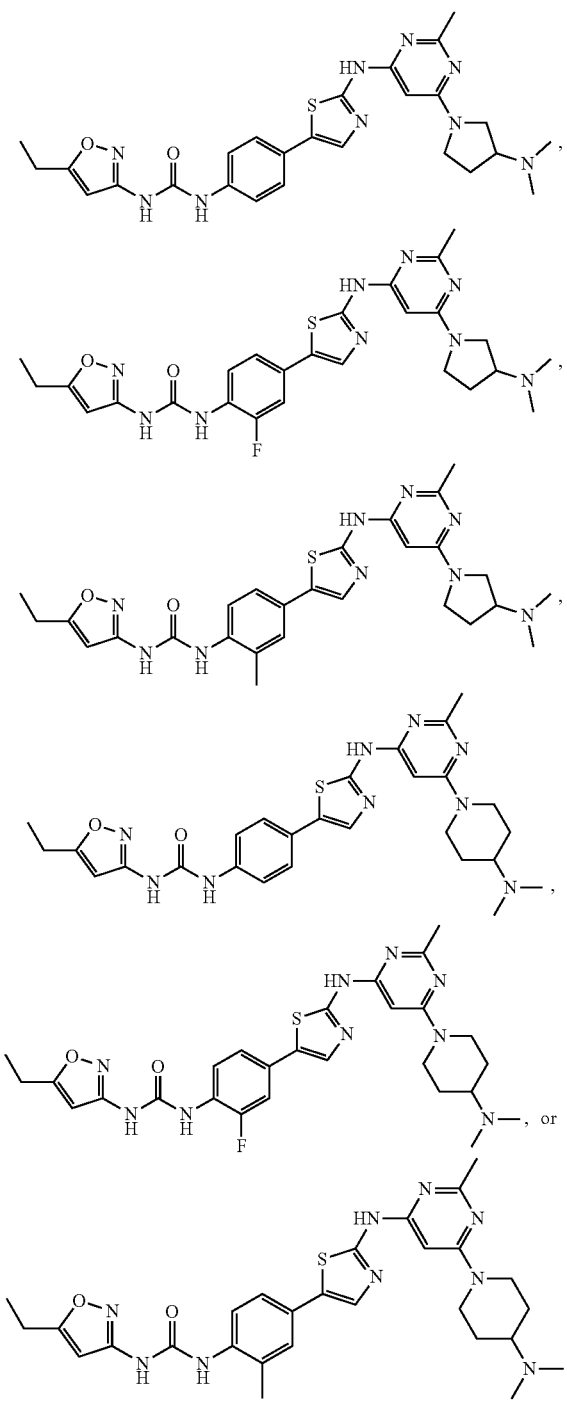

17. The compound of claim 13, wherein
Y is NR$_d$, in which R$_d$, together with R$_a$ and the nitrogen atoms bonded to R$_d$ and R$_a$, is C$_{3-10}$ heterocycloalkyl;
R$_2$ is —CH$_2$CH$_2$R$_e$, in which R$_e$ is halo; and
R$_3$ is H, halo, C$_{1-6}$ alkyl, or C$_{3-10}$ cycloalkyl.

18. The compound of claim 17, wherein R$_d$, together with R$_a$ and the nitrogen atoms bonded to R$_d$ and R$_a$, is piperazinyl.

19. The compound of claim 18, wherein R$_1$ is —CH$_3$.

20. A compound wherein the compound is

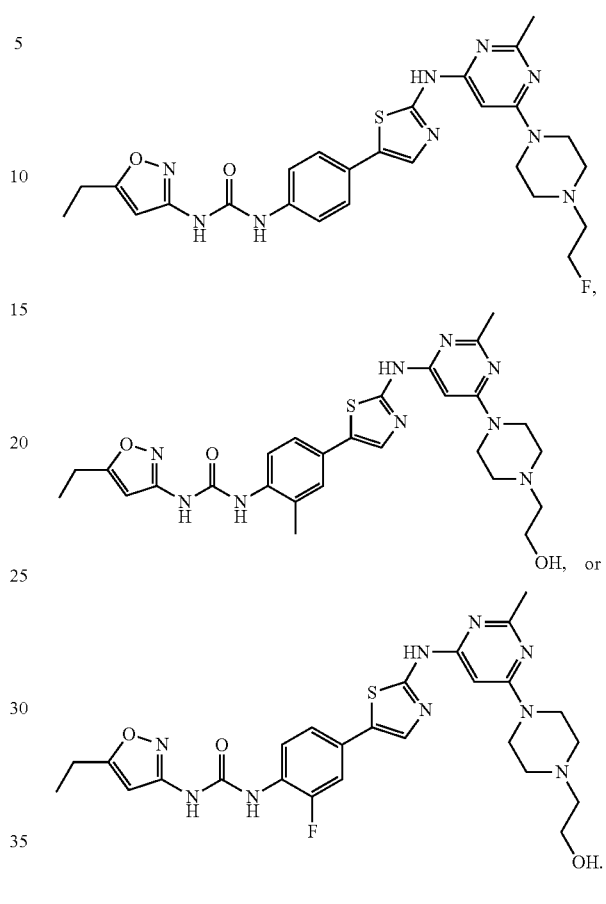

21. The compound of claim 18, wherein R$_1$ is —SCH$_3$.

22. A compound wherein the compound is

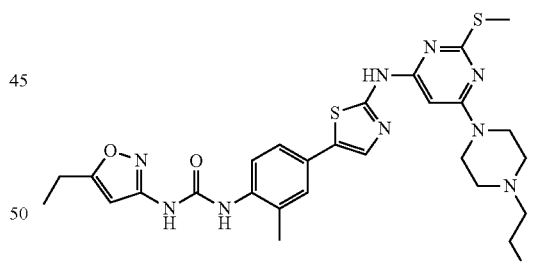

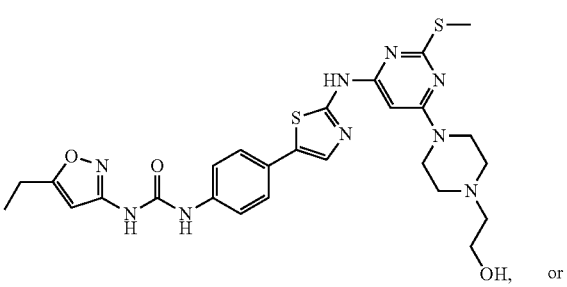

-continued
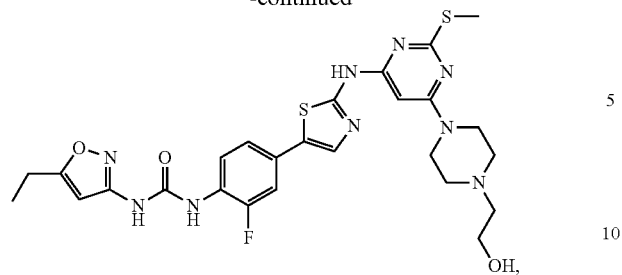
* * * * *